United States Patent
Dietz et al.

[19]

[11] Patent Number: 6,102,867
[45] Date of Patent: Aug. 15, 2000

[54] SHEATH AND METHODS OF ULTRASONIC GUIDANCE OF BIOPSY AND CATHETER INSERTION

[75] Inventors: Dennis R. Dietz, Littleton; Joseph V. Ranalletta, Englewood; Eckehart Zimmermann, Palmer Lake, all of Colo.

[73] Assignee: Tetrad Corporation, Englewood, Colo.

[21] Appl. No.: 09/253,745

[22] Filed: Feb. 22, 1999

Related U.S. Application Data

[62] Division of application No. 08/377,620, Jan. 25, 1995, Pat. No. 5,597,479, and a division of application No. 08/798,633, Feb. 11, 1997, Pat. No. 5,931,787.

[51] Int. Cl.[7] .................................................. A61B 8/12
[52] U.S. Cl. ........................................ 600/461; 600/463
[58] Field of Search .................................... 600/439, 461, 600/463, 471

[56] References Cited

U.S. PATENT DOCUMENTS

| | | |
|---|---|---|
| 4,742,829 | 5/1988 | Law et al. . |
| 4,759,348 | 7/1988 | Cawood . |
| 4,877,033 | 10/1989 | Seitz, Jr. . |
| 4,911,173 | 3/1990 | Terwilliger . |
| 5,070,879 | 12/1991 | Herres . |
| 5,088,500 | 2/1992 | Wedel et al. . |
| 5,090,414 | 2/1992 | Takano . |
| 5,261,409 | 11/1993 | Dardel . |
| 5,335,663 | 8/1994 | Oakley et al. . |
| 5,443,457 | 8/1995 | Ginn et al. . |
| 5,469,853 | 11/1995 | Law et al. . |

FOREIGN PATENT DOCUMENTS 0446645  2/1991  European Pat. Off. .

*Primary Examiner*—Francis J. Jaworski
*Attorney, Agent, or Firm*—Michael de Angeli

[57] ABSTRACT

A sheath for receiving an ultrasonic probe and for defining the relative position of the probe with respect to a biopsy gun or a rigid needle is used for precise placement of the biopsy gun or needle tip in a structure. The sheath may comprise a keyhole-shaped slot for placement of a rigid needle through a puncture separate from a surgical port through which the sheath itself and the probe are introduced. A flexible catheter can thus be placed in a structure, using the ultrasonic probe to monitor its placement, followed by removal of the probe sheath and surgical port, leaving the catheter in place.

8 Claims, 3 Drawing Sheets

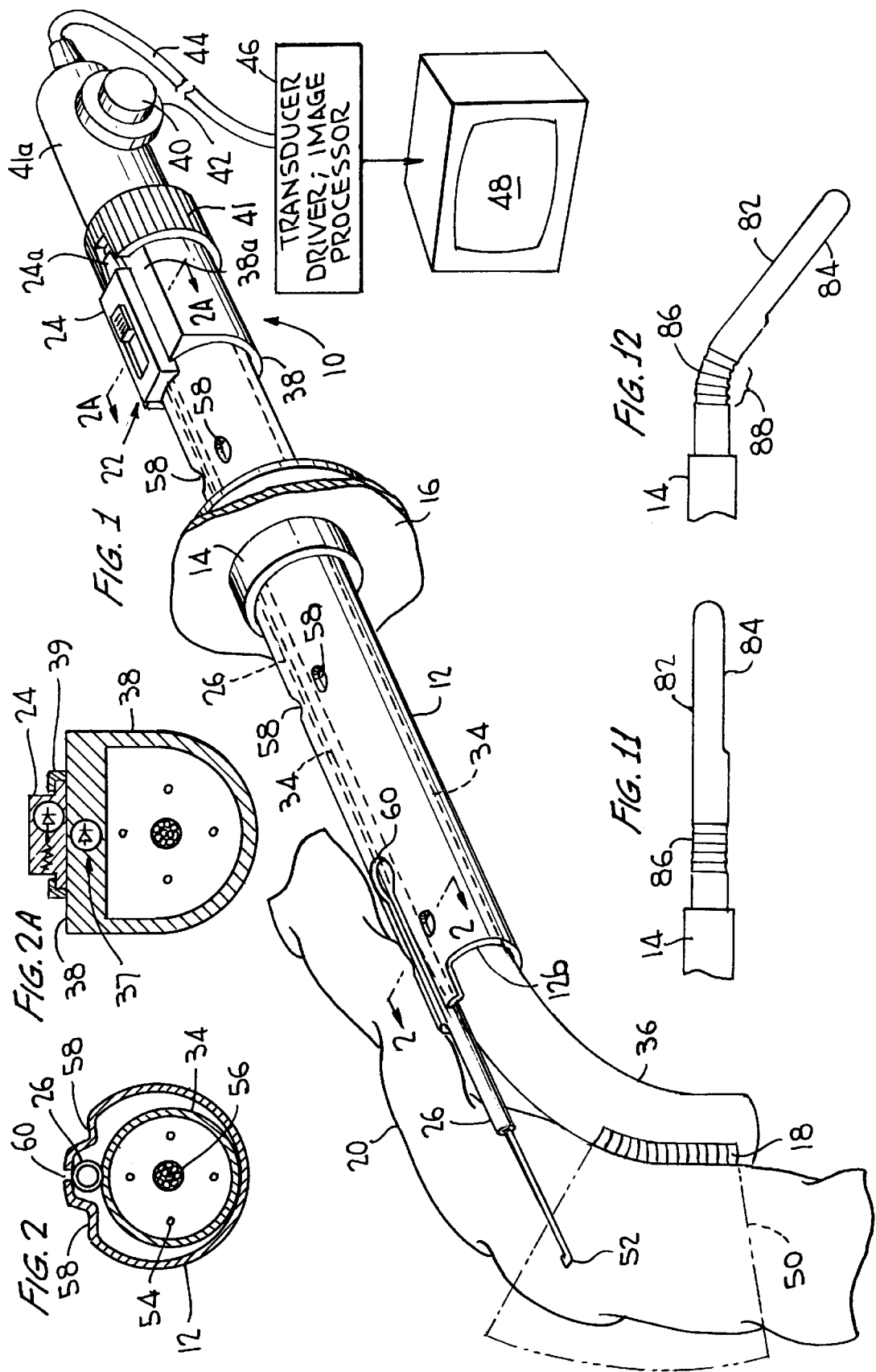

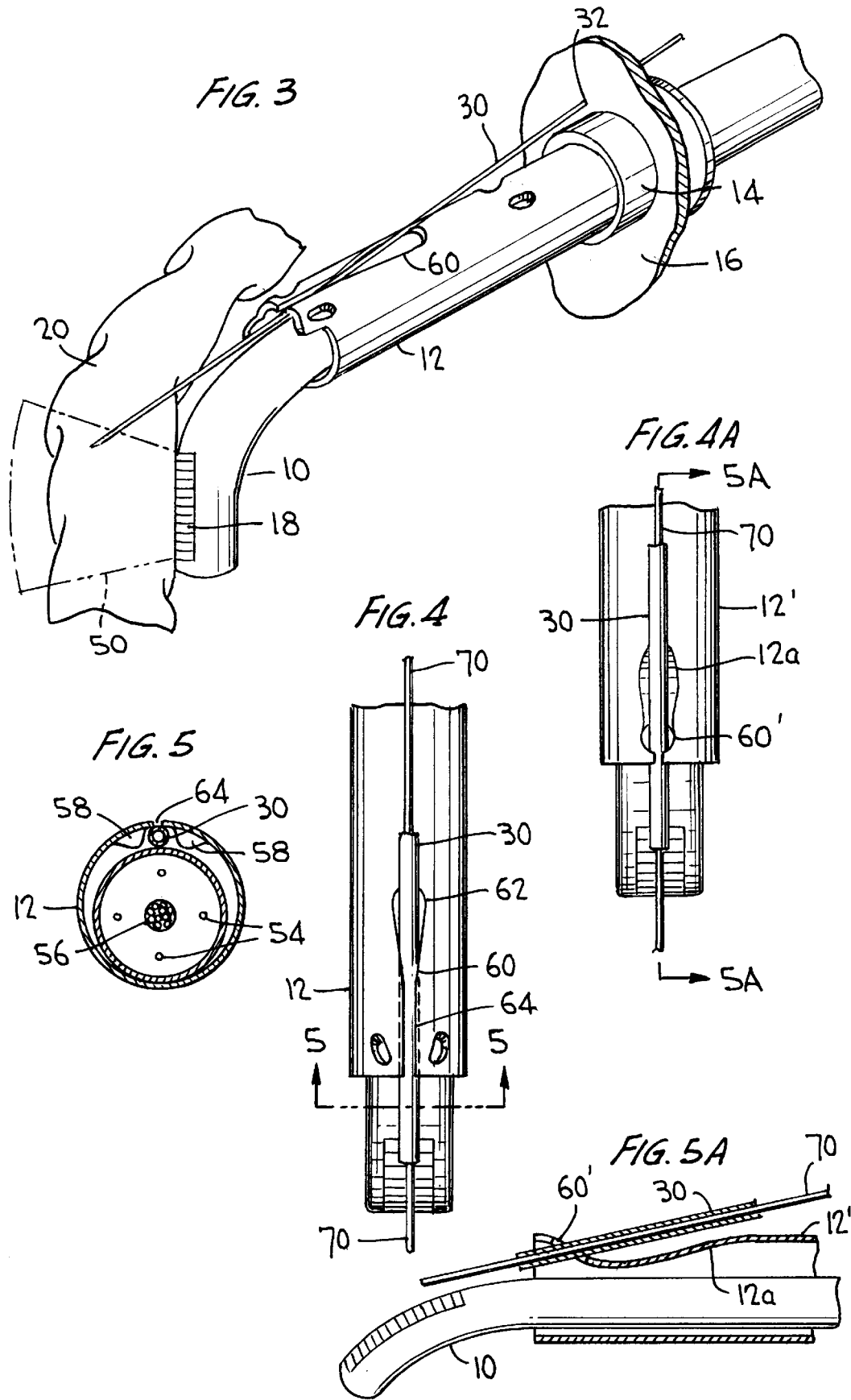

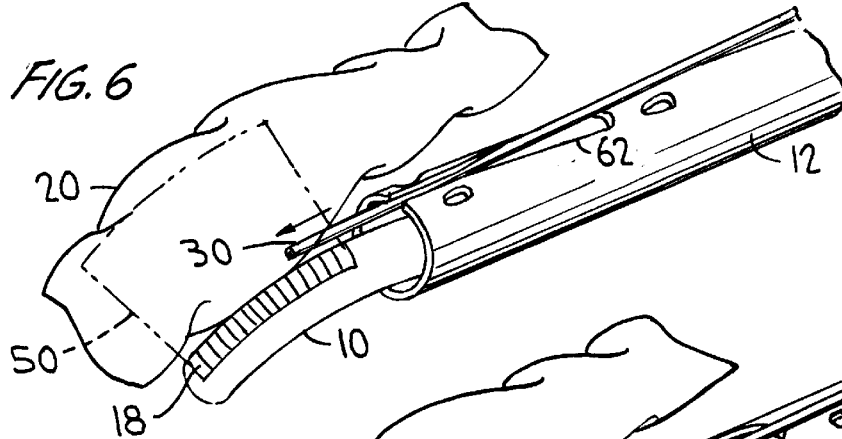
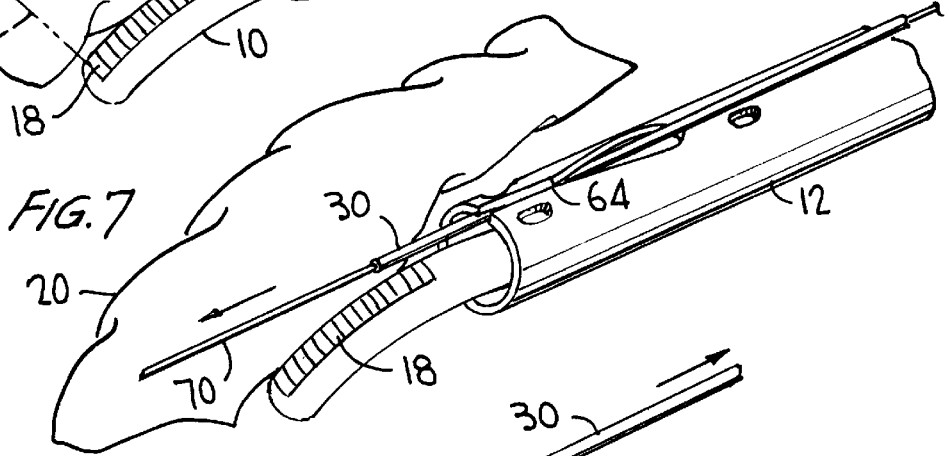
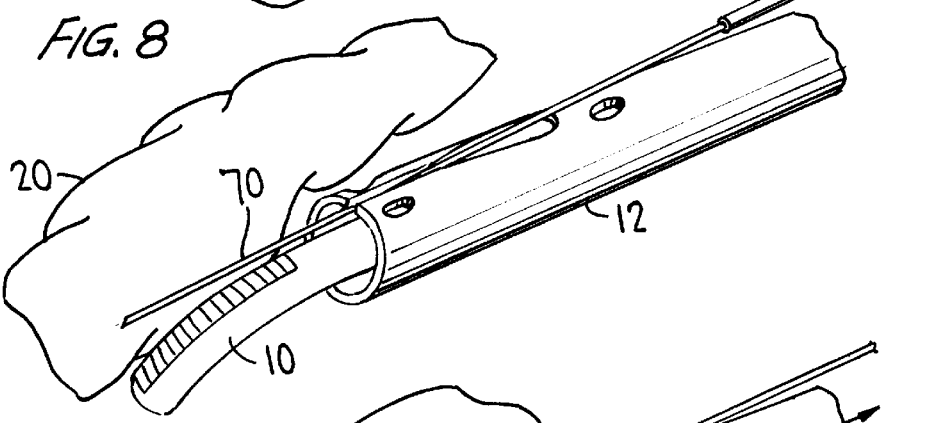
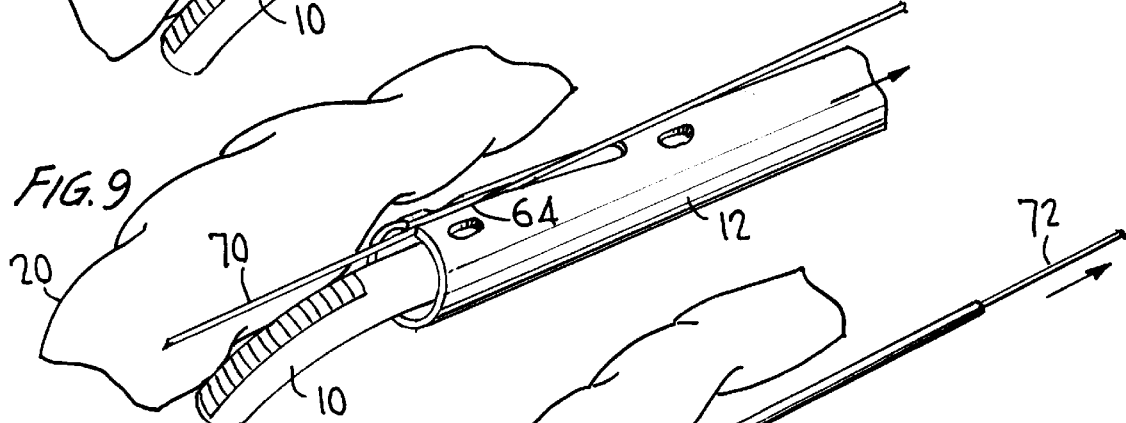
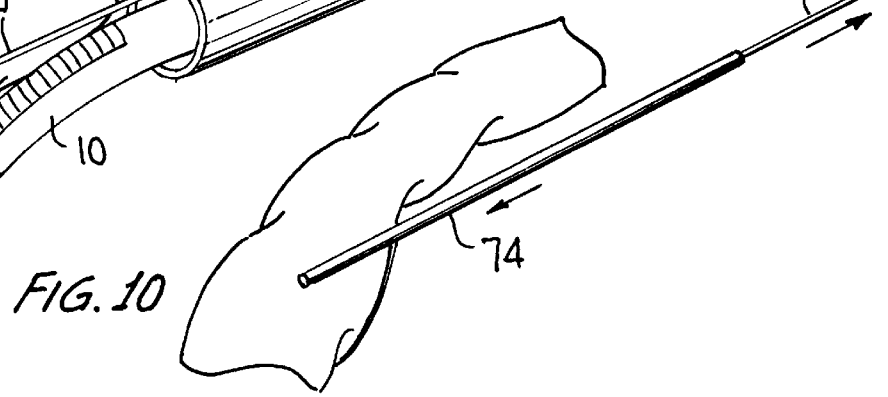

SHEATH AND METHODS OF ULTRASONIC GUIDANCE OF BIOPSY AND CATHETER INSERTION

This is a divisional application of application Ser. No. 08/377,620 filed Jan. 25, 1995, and now U.S. Pat. No. 5,597,479, and also is a div. of Ser. No. 08/798,633 filed Feb. 11, 1997 and now U.S. Pat. No. 5,931,787.

FIELD OF THE INVENTION

This invention relates to use of ultrasonic probes for precise guidance of biopsy guns and other surgical instruments, and for placement of catheters or other members at desired locations in the body of a patient.

BACKGROUND OF THE INVENTION

The use of ultrasonic imaging techniques to obtain visible images of structures is increasingly common, particularly in medical applications. Broadly stated, an ultrasonic transducer, typically comprising a number of individually actuated piezoelectric elements, is provided with suitable drive signals such that a pulse of ultrasonic energy travels into the body of the patient. The ultrasonic energy is reflected at interfaces between structures of varying acoustic impedance. The same or a different transducer detects the receipt of the energy and provides a corresponding output signal. This signal can be processed in known manner to yield an image, visible on a display screen, of the interfaces between the structures and hence of the structures themselves.

Numerous prior art patents discuss the use of ultrasonic imaging in combination with specialized surgical equipment in order to perform very precise surgical procedures. For example, a number of patents show use of ultrasonic techniques for guiding a "biopsy gun", i.e., a instrument for taking a tissue sample from a particular area for pathological examination, for example, to determine whether a particular structure is a malignant tumor or the like. Similarly, other prior art patents discuss use of ultrasonic imaging techniques to assist in other delicate operations, e.g., removal of viable eggs for in vitro fertilization, and for related purposes.

For example, U.S. Pat. No. 5,261,409 to Dardel shows a system for Doppler measurement of blood flow. An ultrasonic beam is reflected so as to be coaxial with a needle introduced to a vein, at an angle to the axis of the transducer itself.

Takano U.S. Pat. No. 5,090,414 shows a system wherein a "stab needle", i.e., a biopsy needle, is mounted parallel to an ultrasonic probe. The transducer pivots to generate a fan-shaped beam, broadening the field of view.

Wedel et al U.S. Pat. No. 5,088,500 show an ultrasonic probe to be mounted on a physician's finger. The mount is provided with a guide for medical instruments, e.g., for biopsy or the like.

Terwilliger U.S. Pat. No. 4,911,173 shows a biopsy needle pivoted with respect to an ultrasonic probe, so that its distal tip can be moved into the field of view of the ultrasonic transducer.

Seitz U.S. Pat. No. 4,877,033 shows a combination instrument for transvaginal ultrasound procedures. A molded plastic guide receives both the ultrasonic probe and the aspiration instrument used to remove eggs for in vitro fertilization purposes.

Law et al U.S. Pat. No. 4,742,829 is directed to a instrument for generally similar processes. A guide for a biopsy needle is attached to the barrel of an ultrasonic probe, again for imaging of transvaginal procedures.

U.S. Pat. No. 5,335,663 to Oakley et al and a continuation-in-part thereof, now U.S. Pat. No. 5,469,853 to Law et al, both commonly assigned with the present application, teach combinations of ultrasonic probes and sheaths therefor. In particular, the Law '853 patent shows a sheath having internal lumens for accommodating a biopsy gun in spaced parallel relation to an ultrasonic probe so that the probe can be used to image and identify the tissue being sampled. The sheath is circular, so as to be sealed to a conventional surgical port. Sealing is frequently desired in performing procedures in the abdominal cavity, in order that compressed gas can be introduced to the surgical site, inflating the cavity somewhat and providing the surgeon with room to work. The ultrasonic probe shown in the '853 patent is articulated, so that the transducer can be disposed at an angle to an organ, enabling certain additional flexibility in selection of tissue for biopsy and imaging purposes. See FIG. 40.

EP application 0 446 645 of Kopek shows a curved ultrasonic transducer for imaging the prostate. A biopsy needle can be coupled to the probe for sampling tissue thought possibly to be diseased.

Articulated ultrasonic probes wherein the transducer is also rotatable about its axis are shown in detail in commonly assigned U.S. Pat No. 5,413,102 to Oakley et al.

Of further general interest is U.S. Pat. No. 5,070,879 to Heres relating to ultrasonic imaging generally. Commonly assigned U.S. Pat. No. 5,503,152 to Oakley et al teaches further specifics of ultrasonic signal processing techniques for image generation.

U.S. Pat. No. 4,759,348 to Cawood teaches an optical endoscope coupled with a biopsy needle or the like.

Ginn et al U.S. Pat. No. 5,443,457 shows a technique for placement of a relatively soft catheter, so as to enable drug delivery to a specified desired region of a patient's body. A relatively rigid guide wire is first placed in the tissue of interest, and a soft catheter is then slid over the guide wire.

Objects and Summary of the Invention

The present invention is directed to further improvements in use of ultrasonic probes for both biopsy and also for placement of catheters or the like in specified regions of the patient's body. In particular, it is an object of the invention to provide a single sheath which can be introduced through and sealed to a surgical port, and then used to guide an ultrasonic probe and a biopsy gun, as shown in the Law et al '853 patent, but which can also be used to guide a rigid member, such as an elongated needle, introduced through a separate puncture. As will appear in detail below, in this way, the combination of an ultrasonic probe and sheath can be used both to perform very precise biopsy, or to place the tip of a catheter to a desired area.

The same combination of probe and sheath can be used for both of these and numerous other purposes. In particular, the probe and sheath can be used for precise placement and use of rigid elongated instruments other than biopsy guns.

It is a further object of the invention to provide a sheath designed such that after a catheter has been placed as desired, the probe and sheath can be removed, so that the surgical port through which the ultrasonic probe is inserted can be removed and the incision closed, or used for other purposes.

It is a further object of the invention to provide a reusable sheath which can be readily sterilized, and in particular, to avoid small-diameter elongated tubular guide members, which are difficult to sterilize.

Further objects of the invention include provision of means preventing removal of the ultrasonic probe from the surgical port while articulated; several surgical ports now on the market have very sharp distal edges and can damage the ultrasonic probe if a surgeon seeks to remove the probe before straightening it.

A further object of the invention is to provide cooperating structure for an articulable and optionally rotatable ultrasonic probe, sheath, and biopsy gun, such that the transducer cannot be bought into contact with the gun, reducing damage to the probe.

A further object of the invention is to provide a combination of a biopsy gun and ultrasonic probe to be operated together and provided with cooperating mounting means, such that the effective operating point of the biopsy gun is automatically communicated to the control circuitry of the probe, so that the position of the biopsy can be precisely targeted on an image of the site.

Other aspects and objects of the invention will appear as the discussion below proceeds.

According to the present invention, a sheath is provided for being received within and sealed to the lumen of a surgical port. The sheath itself has a lumen which receives the ultrasonic probe and biopsy gun. The sheath also includes means for locating a needle for precise placement of a catheter or the like.

Preferably, the sheath is formed to comprise a number of pairs of indentations disposed on either side of a line extending along its surface. The indentations locate the biopsy gun with respect to the ultrasonic probe and also space the ultrasonic probe away from the side of the sheath in which the indentations are formed.

Where the sheath is to be used with a needle for placement of a catheter or the like, a keyhole-shaped slot open at the distal end of the sheath is provided between the pairs of indentations. The keyhole-shaped slot has a wider portion spaced from the distal end of the sheath which is wide enough to receive a relatively rigid needle, and a narrower portion just wide enough to pass the smaller catheter. The needle is inserted through a separate skin puncture spaced away from the surgical port. When the needle enters the wide portion of the keyhole-shaped slot, its tip enters the field of view of the ultrasonic transducer; the ultrasound image is then used to assist in placement of the tip of the needle at a desired location. A catheter can then be slid down the lumen of the needle and left in place while the rigid needle, ultrasonic probe, sheath, and surgical port are removed. Alternatively, a guide wire can be passed down the lumen of the needle and left in place for subsequent placement of a relatively larger catheter.

The sheath is typically provided with a keying arrangement to locate it radially with respect to the ultrasonic probe so that the surgeon can employ tactile feedback when placing the tip of the needle in the keyhole-shaped slot. The sheath may also be provided with a cut-out allowing bending of the articulated ultrasonic probe only in the direction away from the needle or biopsy gun, to prevent damage to the ultrasonic transducer. The mounting bracket of the sheath may limit the motion of the knob controlling the articulation preventing damage to the transducer. If the transducer is also rotatable about its axis, a hole or notch in a ring for receiving the needle may be provided on the handle controlling the rotation mechanism. The handle cooperates with the sheath, so as to ensure that the transducer face is rotated so as to be perpendicular to the plane of articulation, and in the same plane as the needle, when the needle is inserted through the hole or notch.

The handle of the biopsy gun is received by a cooperating mounting structure on the handle of the probe, ensuring their correct relative positions. The handle of the biopsy gun may also cooperate with the handle of the probe to limit the operation of articulated and rotatable probes, preventing damage to the transducer, and to ensure their relative orientation. Cooperating encoding devices identifying the gun to the control circuitry can be provided, for example, allowing the target of the gun to be displayed in the image of the surgical site. The sheath of the ultrasonic probe may include several layers of materials of contrasting colors to indicate whether the sheath has been damaged upon withdrawal from the surgical port, or may be provided with means positively preventing removal while articulated.

BRIEF DESCRIPTION OF THE DRAWINGS

The invention will be better understood if reference is made to the accompanying drawings, in which:

FIG. 1 shows a generally schematic three-dimensional perspective view of an ultrasonic probe in a sheath with a biopsy needle and illustrates the connection of the probe to related components of an ultrasonic imaging system;

FIG. 2 shows a cross-section along line 2—2 of FIG. 1;

FIG. 2A shows a cross-section along line 2A—2A of FIG. 1;

FIG. 3 shows a view comparable to FIG. 1, eliminating common components, and showing use of the sheath to place a catheter;

FIG. 4 is a elevational view of the tip of the sheath, showing the keyhole slot in detail;

FIG. 4A is a comparable view showing a second embodiment of the tip of the sheath;

FIG. 5 is a cross-section along line 5—5 of FIG. 4;

FIG. 5A is a cross-section along line 5A—5A of FIG. 4A;

FIGS. 6,7,8,9 and 10 are views generally comparable to a portion of FIG. 3, showing steps in the sequence of placement of a catheter according to the method of the invention; and FIGS. 11 and 12 show comparative views of one embodiment of an articulated ultrasonic transducer in its normal and articulated conditions, illustrating a method for preventing removal of the probe from the sheath while articulated.

DESCRIPTION OF THE PREFERRED EMBODIMENTS

FIGS. 1 and 3 show perspective views of an ultrasonic probe 10 fitting within a lumen of a sheath 12, inserted through a surgical port 14 installed in a puncture made in the skin 16 of a patient, so as to juxtapose the transducer 18 of the probe 10 to an organ 20 or other structure to be examined. Surgical port 14 is of the conventional type used for various minimally-invasive surgical procedures, and has a circular lumen. Sheath 12 is circular in cross-section, so as to be sealed to the lumen of port 14; this allows compressed gas to be retained in the vicinity of the surgical site as needed.

The surgical port 14 and probe 10 are identical in both FIGS. 1 and 3. However, in FIG. 1, the probe is illustrated as used to image the placement of a biopsy gun 22 including a handle portion 24 and a generally cylindrical portion 26 inserted within sheath 12, while FIG. 3 illustrates the use of the probe in precise placement of a rigid, elongated needle 30 having been inserted through a separate puncture 32 in the skin 16.

A single design of sheath 12 may be used for practice of both processes or specialized sheaths may be provided for both purposes. For example, if it is preferred to sterilize and reuse the sheath, it will normally be made useful for both purposes, while a disposable version may be specialized. It is generally an object of the invention to employ the same design of sheath 12 and the same ultrasonic probe 10 in both uses of the system of the invention. Therefore, a description of one use of the sheath should be construed as relating equally to the other unless explicitly indicated to the contrary.

Accordingly, referring now specifically to FIG. 1, it will be observed that the ultrasonic probe 10 includes an elongated cylindrical portion 34, an articulated portion 36, shown curved, at the end of which transducer 18 is mounted, and a handle portion 38. The handle portion 38 includes control apparatus exemplified by concentric knobs 40, 42 for controlling the articulation of the probe. Rotation of the transducer about its axis may also be provided, operated by rotatable ring 41. The detailed structure of the probe and the control arrangements thereof may be as discussed in further detail in commonly assigned U.S. Pat. No. 5,413,102, incorporated by reference herein. The transducer 18 is connected by signal wires 56 (FIG. 2) and a cable 44 to control and image processing electronics 46, which drive display 48 to provide an image of objects in the field of view 50 of the transducer 18.

According to an important aspect of the invention, the elongated portion 26 of biopsy gun 22 is passed through the same surgical port 14 and lumen of sheath 12 as is the ultrasonic probe 10. Other rigid elongated instruments, e.g., needles, needle holders, rigid catheters, and guide wires, can similarly be introduced while monitoring their positions. Reference herein to "biopsy guns" should be understood to refer to all such elongated instruments unless otherwise indicated, while reference herein and in the following claims to "rigid elongated instruments" should be understood to include biopsy guns as well as all other types of instruments introduced through the lumen of the sheath. Transducer 18 images the field of view 50 and shows the tip 52 of the biopsy gun, e.g., penetrating the organ 20 to be examined. When the image shown on display 48 indicates that the tip of the gun 52 is at the appropriate point, the gun is fired by operation of the handle portion 24, cutting a section of tissue free from the organ 20 and retracting it within the cylindrical portion 26 of the biopsy gun for withdrawal, pathologic examination and the like. The detailed structure and operation of biopsy guns are well known, and are further discussed in the commonly-assigned Law '853 patent.

FIG. 2 shows a cross-section along line 2—2 of FIG. 1 and illustrates the sheath 12, within which fit the cylindrical portion 34 of the probe 10 and the cylindrical portion 26 of the biopsy gun 22. Within the cylindrical portion 34 of probe 10 are illustrated control wires 54 for controlling the articulation of the probe, and signal wires 56 for carrying drive and return signals to and from the transducer, shown in a strictly schematic fashion. Further details of representative signal processing electronics and control arrangements of the articulated ultrasonic probe are found in the commonly-assigned patents discussed above.

In order that the surgeon can determine by feel the relative orientation of the biopsy gun and transducer, and so that the probe can be useful while permitted to articulate only in certain desired directions, as discussed in detail below, it is important that the gun, probe, and sheath all be reliably oriented. To this end, the relative radial positions of the biopsy gun 22 and the probe 10 may be maintained as illustrated in FIGS. 2 and 2A. As shown in FIG. 2, the cylindrical portion 26 of the biopsy gun fits between pairs of inward protuberances or "dimples" 58 formed on either side of a line extending the length of sheath 12, confining cylindrical portion 26 to the space between the dimples 58 and the probe 34. The relative positions of the biopsy gun and probe could also be maintained by provision of separate lumens within sheath 12, as discussed in the Law '853 patent at col. 20, line 64. However, such separate lumens would be relatively difficult to sterilize, while the simple dimpled sheath is easily disinfected. The dimples also urge probe 34 away from the side of the sheath 12 in which the dimples 58 are formed.

As can be seen in FIGS. 1 and 2, a keyhole-shaped slot 60 is also formed in the sheath along the line extending between the pairs of dimples 58, for use of the sheath in placement of a needle, e.g., for placement of a catheter, as discussed in detail below in connection with FIG. 3. More specifically, if the sheath 12 is to be used only with the biopsy gun, keyhole slot 60 can be omitted; if the same sheath is to be useful for placement of either the biopsy gun or with a rigid needle for placement of a catheter, then the slot 60 is provided in the sheath as well.

As noted above, a single design of sheath 12 may be used for both purposes, or specialized sheaths may be provided for each. For example, if it is preferred to sterilize and reuse the sheath, it will normally be designed to be useful for both purposes, while a disposable version may be specialized. When the sheath is be reusable and thus sterilized, it may be formed of stainless steel tubing, e.g., 0.3 mm wall thickness; where the sheath is intended to be disposable, it can be molded of a biocompatable plastic material.

The relative orientation of the probe 10, the sheath 12, and the biopsy gun 22 is made positive by providing cooperating members at their distal ends. See FIG. 2A. In the embodiment shown, the handle portion 24 of the biopsy gun 22 and the handle portion 38 of the probe meet at juxtaposed flat surfaces, essentially as discussed in the commonly-assigned Law '853 patent, and are provided with cooperating mounting structure 39. The cylindrical portion 34 of the probe is offset with respect to handle portion 38, so that the outer surface of cylindrical portion 34 is generally tangent to the flat surface 38a to which the handle portion 24 of the biopsy gun 22 is mounted. Accordingly, the cylindrical portions of probe 10 and gun 22 are closely juxtaposed and parallel to one another. Numerous other arrangements whereby the gun 22 and probe 60 may be reliably fixed with respect to one another will be apparent to those of skill in the art, and are within the scope of the invention.

The mating planar surfaces of biopsy gun 22 and probe 10 may conveniently be employed to carry cooperating coding means whereby various salient characteristics may be communicated from one to the other upon their assembly. For example, certain conventional biopsy guns take a tissue sample 15 mm from their tips when fired, while others may sample only 5 mm from their tips. If this characteristic of the gun is communicated to the image control circuitry 46 by encoding means when the gun is mounted to the probe, a target indicating the point at which the sample will be taken can be superimposed on the image of the organ visible to the surgeon on display 48, ensuring biopsy of the tissue of principal interest.

These and other characteristics of the gun can be communicated to the display circuitry 46 by adaption of any of a number of known techniques. For example, the handle portion 24 of gun 22 may be provided with a magnetic stripe and the handle portion 38 of probe 10 with a cooperating reader. Another possibility would be to provide a series of light-emitting diodes arranged in an encoded pattern on the gun, and a photo transistor on the probe to detect their presence, as illustrated schematically at 37. Other cooperative encoding arrangements are within the skill of the art.

The sheath may similarly be keyed to the probe to insure that the biopsy gun 22, sheath 12, and probe 10 are all in fixed radial alignment to one another. For example, the sheath is shown shaped to fit beneath the handle 24 of the biopsy gun, preventing relative rotation thereof. Other arrangements are of course within the scope of the invention. Snap-fitting detents may be provided to secure the components of the assembly together, e.g., when the probe and the biopsy gun have been inserted into the sheath.

As discussed above, it is an object of the invention to preclude the transducer 18 from impacting the biopsy gun 26, to prevent damage of the transducer 18. In order to prevent this, the sheath may be formed with a cut-away portion indicated generally at 12a, which allows articulation of the probe 10 only in the direction away from the biopsy gun 22; that is, the side of the sheath along which the biopsy gun fits extends past the beginning of the articulable portion 36 of the probe, precluding the probe from bending upwardly and impacting the transducer 18 against the biopsy gun 26.

Other means of preventing articulation of the probe so as to prevent impacting the transducer against the biopsy gun may also be provided, such as stops preventing rotation of controls 40, 42, or other physical limitation on operation of the articulation of the probe. For example, as shown in commonly-assigned U.S. Pat. No. 5,413,102, additional flexibility is provided if the transducer is rotatable, e.g., by rotation of ring 41. To prevent rotation of the transducer when used with a biopsy gun 22, both to ensure that the transducer is located at a known radial position fixed with respect to the position of the gun 22, and to prevent damage to the transducer by impacting the biopsy tip 52, the handle 24 of gun 22 may include a tang 24a fitting into a slot 41a in ring 41, securing the transducer in a fixed radial position. Where the transducer is to be used to place a needle precisely, as in the FIG. 3 embodiment of the invention, ring 41 can be formed to extend radially outwardly from the handle of the probe. A slot or hole can then be provided in the ring through which the needle must extend; this ensures that the transducer is properly aligned, that is, so that the needle is in the field of view of the transducer.

FIG. 3 shows, as mentioned, a view comparable to FIG. 1, but illustrating use of the ultrasonic probe 10 and sheath 12 to place precisely the tip of an elongated relatively rigid needle 30 inserted through a separate skin puncture 32. As can be seen in FIG. 3 and in more detail in FIG. 4, the needle 30 fits within a wider first portion 62 of an elongated keyhole-shaped slot 60, but is too wide to pass through a second narrower portion 64 terminating at the distal end of the sheath 12. In use, a surgeon inserts needle 30 through puncture 32, and then through the wider portion 62 of the slot 60, so that its tip emerges in the field of view 50 of the transducer 18, as shown. (Typically the surgeon will also be able to view the interior of the body cavity on an optical endoscope (not shown) which will be of assistance in causing the needle to enter the larger portion of the slot 60.) When the tip of the needle enters the field of view 50 of the transducer 18, the surgeon will be able to view its position within organ 20 on monitor 48 (FIG. 1), enabling precise placement of the tip of the needle 30 at a particular point desired in organ 20. The discussion below of FIGS. 6 through 10 illustrates the steps in the placement of a flexible catheter at the precise point in organ 20, followed by removal of the probe, sheath, and port.

Further details shown in FIG. 4 include the inward protrusions or dimples 58, also shown in the end view of FIG. 5. The dimples 58 locate the probe with respect to the sheath and space it from the keyhole-shaped slot 60, so that needle 30 does not impact transducer 18. Again, other means of spacing the probe from the needle 30 might be provided.

The keyhole-shaped slot 60 shown in FIGS. 1–4, 5, and 6–10 is essentially formed by removal of a portion of the sheath. In an alternative embodiment, shown in FIGS. 4A and 5A, an indentation 12a is formed in the tubular surface of the sheath 12', adjacent the proximal portion of the slot 60', to assist in guiding the tip of a needle into the slot. Slot 60' is relatively truncated as compared to the elongated slot shown in the other figures but again includes a wider portion to pass the relatively rigid needle 30 and a relatively narrow portion to pass the catheter 70. The indentation provides a "target" for the tip of the needle. As the indentation 12a meets the edge of the slot below the surface of the sheath, as the needle is urged forwardly along the indentation, the tip of the needle is guided into the slot, simplifying its insertion. In this embodiment, the indentation 12a precludes use of the sheath 12' with a biopsy probe. Other embodiments of the slot providing essentially the same functions described, that is, guiding a relatively larger diameter rigid member into the vicinity of the transducer, and allowing the sheath to be removed while leaving a smaller-diameter, flexible catheter in place, are within the scope of the invention.

A principal reason for location of the tip of needle 30 at a particular point in organ 20 is as a step in placement of the tip of a flexible catheter or similar elongated flexible structure at the precise point desired. For example, a catheter may be thus placed to enable delivery of a drug to a precisely determined point within an organ 20 for various therapeutic purposes. The method of the invention can be used similarly to place components for repetitive blood sampling, or a sensor or stimulating electrodes connected by flexible wires to external circuitry. A relatively flexible catheter or like structure thus placed precisely according to the invention can be left in place for an extended time without undue discomfort. By comparison, it is highly undesirable to leave a rigid needle or other structure in place over a long period of time, as this restricts the patient's freedom of movement, can cause great pain, may cause tissue damage, and the like.

It is therefore an object of the invention and more specifically the function of sheath 12 to assist the surgeon in placing the tip of a rigid needle 30 at an exact spot in the organ desired, using the image provided by transducer 18 to ensure that the tip of the needle is placed precisely, and then to place the tip of a flexible catheter in the desired spot. Placement of the catheter or other structure is then followed by removal of rigid needle 30, removal of probe 10 and sheath 12 from surgical port 14, removal of the port 14, and closure of the puncture wound through which the port 14 entered, leaving only the flexible catheter 70 in place.

A The steps in this process are shown in FIGS. 6–10. FIG. 6 corresponds substantially to FIG. 3, and illustrates the sheath 12 in place, and the probe 10 and transducer 18 protruding therefrom so as to image the organ 20. A rigid needle 30 is inserted through a separate skin puncture 32 spaced away from port 14 (FIG. 3) and through the wide portion 62 of the slot 60. The tip of needle 30 then enters the field of view 50 of transducer 18, so that its position can be viewed on monitor 48 (FIG. 1) enabling its accurate placement. When the needle 30 is in place, a second smaller member, typically a flexible catheter 70, or a guide wire, is passed down the lumen of the needle 30 as shown in FIG. 7. The catheter 70 is of a diameter less than the width of the narrow portion 64 of the slot 60. This allows the sheath subsequently to be removed from the surgical port while leaving catheter 70 in place. Before this can be performed, however, needle 30 must be removed, as indicated in FIG. 8, leaving catheter 70 in place. Typically, catheter 70 is inserted without a proximal terminal fitting, enabling the needle to be removed from its proximal end. A suitable terminal fitting (not shown) is then applied to catheter 70. Subsequently, as shown in FIG. 9, the probe and sheath are removed, while the catheter 70 slides along the narrow portion 64 of the slot 60, in order to remain at the desired position in organ 20. The surgical port 14 can then be removed and the incision closed. The catheter 70 can then be used for supply of drugs to the precise position desired, for blood withdrawal or infusion, or for other various purposes. A series of several catheters could be placed similarly.

In a further aspect of the invention, if it is desired to put a relatively large diameter catheter in place, a guide wire may be slid down the lumen of the needle, in a step corresponding to that shown in FIG. 7, followed by removal of the needle, as shown in FIG. 8, and removal of the sheath 12 and probe 10, as shown in FIG. 9. A larger diameter catheter 74 can then be placed over the guide wire 72, and the wire 72 removed, both as indicated in FIG. 10.

It will be appreciated that electrical wires for muscle stimulation, electrodes for sensing nervous impulses or chemical conditions, or other members could similarly be placed in very precise positions in organs or other bodily structures using the apparatus and techniques discussed. In each case, the invention allows a relatively flexible structure to be inserted through a small puncture and left in place, while the relatively large and cumbersome probe needed for precise placement, together with the surgical port, sheath, and rigid needle, can all be withdrawn and the larger puncture required for their introduction closed properly.

It is desirable that the sheath and probe combination according to the invention, whether used with a biopsy gun or other rigid elongated instrument extending parallel to the probe in the sheath, or with a separate needle introduced through a separate puncture, should be useful with surgical ports already in common use. Such surgical ports are available in 5, 10, and 12 mm inside diameters. It is within the skill of the art to fabricate the other components of the combination according to the invention, in particular sheath 12, to fit within the preexisting surgical ports and form a substantially gas-tight seal therewith. However, it will also be appreciated by those of skill in the art that such surgical ports commonly have very sharp edges at their circular distal openings. Articulated ultrasonic probes in particular are susceptible to being cut on these sharp edges; if a surgeon attempts to withdraw an articulated probe from the port without straightening it out, the probe is likely to suffer damage. Several expedients according to the invention may be adopted to prevent such damage, or to provide the user with a clear indication that damage has occurred, such that the probe can be repaired as necessary. FIGS. 11 and 12 show straight and articulated versions of the same probe, illustrating one expedient useful in preventing such damage.

These figures illustrate a probe 80 including a protective articulated section 86 which is constructed so as to assume a larger diameter when the probe is articulated, as illustrated in FIG. 12. Accordingly, if the surgeon attempts to withdraw the probe 82 from the portal 80 without straightening it out, the raised portion 88 will abut the end of the tubular surgical port 14, preventing damage to other portions of the probe. Obviously, the portion 86 may be made replaceable in the event of damage.

Another expedient within the scope of the invention is to make an outer sheath of the articulated portion of the probe of a first color and an inner material of contrasting color, such that any partial cuts or tears would be clearly visible, indicating that repair or replacement is required. Other expedients are similarly within the skill of the art.

While a preferred embodiment of the invention has been shown and described in detail, numerous alternatives and additions thereto will occur to those of skill in the art and should be considered within the scope thereof where not explicitly excluded by the following claims. Accordingly, the invention is not to be limited by the above exemplary disclosure but only by the following claims.

What is claimed is:

1. A method for placing a distal tip of an elongated flexible member at a desired location in a patient's body, comprising the steps of:

installing a surgical port in a desired portal in said body, said port having a lumen sized to accommodate an ultrasonic probe in a sheath;

placing a tubular sheath in said port, said tubular sheath defining a lumen for receiving an ultrasonic probe and comprising means for guiding a rigid elongated member into the vicinity of the tip of the ultrasonic probe, inserting an ultrasonic probe into said tubular sheath, such that a transducer of said probe is positioned to image said desired location within said body for placement of a distal tip of said elongated flexible member, inserting a distal tip of a relatively rigid elongated tubular member through a skin puncture spaced from said portal, employing said means for guiding to guide said distal tip into the vicinity of said transducer, and thence into a desired position for placement of a distal tip of said elongated flexible member, while employing said transducer to monitor the location of the distal tip of the relatively rigid elongated tubular member, passing a second member along a lumen of said relatively rigid elongated tubular member, such that a tip of said second member is disposed at the desired location of the tip of said elongated flexible member, withdrawing said relatively rigid elongated tubular member while leaving said second member in place, and withdrawing said tubular sheath and ultrasonic probe from said surgical port.

2. The method of claim 1, wherein said means for guiding comprises a keyhole-shaped slot formed in said sheath, said slot being aligned along the axis of said sheath and having a first portion too narrow to pass said rigid elongated member, terminating at a distal end of said sheath, and a second relatively wider portion spaced from said distal end of said sheath and wide enough to receive said rigid elongated member, wherein said step of employing said means for guiding to guide said distal tip of said relatively rigid elongated tubular member into the vicinity of said transducer is performed by passing said elongated tubular member through said relatively wider portion of said keyhole-shaped slot.

3. The method of claim 2, wherein the proximal end of said keyhole-shaped slot is juxtaposed to the distal end of an indentation formed in said tubular sheath, and comprising the further step of employing said indentation to guide the rigid elongated tubular member to a desired position.

4. The method of claim 1, wherein said second member is a tubular catheter.

5. The method of claim 1, wherein said second member is a guide wire, and comprising the further steps of:

sliding a catheter along said guide wire until a distal tip of said catheter is disposed at said desired location, and withdrawing said guide wire.

6. The method of claim 1, wherein said sheath comprises a plurality of pairs of protrusions extending inwardly from the outer surface of said sheath, said pairs of protrusions being located on either side of a line extending along the surface of said sheath and including the axis of elongation of said slot, and said method comprises the further step of employing said pairs of protrusions to guide said probe within the lumen of said sheath while remaining spaced from said slot.

7. The method of claim 1, wherein said ultrasonic probe is controllably articulated, and said method comprises the further step of controllably articulating said probe so as to dispose a transducer of said probe in position to image said desired location within said body.

8. The method of claim 7, wherein a portion of the distal end of said sheath opposite said slot is cut away, and comprising the further step of controllably articulating said probe only away from said relatively rigid elongated member.

* * * * *